United States Patent [19]

Stuart et al.

[11] Patent Number: 5,094,260

[45] Date of Patent: Mar. 10, 1992

[54] PROPORTIONAL VALVE AND PRESSURE CONTROL SYSTEM

[75] Inventors: John M. Stuart, El Toro; Michael H. Peterson, Glendale, both of Calif.

[73] Assignee: Alcon Surgical, Inc., Ft. Worth, Tex.

[21] Appl. No.: 603,502

[22] Filed: Oct. 26, 1990

[51] Int. Cl.⁵ .......................................... G05D 16/20
[52] U.S. Cl. ................................. 137/102; 137/487.5; 137/596.17
[58] Field of Search ............. 137/596.17, 596.2, 487.5, 137/102; 251/129.05

[56] References Cited

U.S. PATENT DOCUMENTS

| | | |
|---|---|---|
| 1,641,561 | 9/1927 | Whidden . |
| 1,959,811 | 5/1934 | Brady et al. . |
| 2,342,770 | 2/1944 | Temple ................... 137/596.2 X |
| 2,504,610 | 4/1950 | Wolf . |
| 2,661,925 | 12/1953 | Barkelew . |
| 2,905,462 | 9/1959 | Christenson .............. 137/596.2 X |
| 3,165,327 | 1/1965 | Cripe ........................ 137/596.17 X |
| 3,222,996 | 12/1965 | Thieme ..................... 137/596.17 X |
| 3,403,700 | 10/1968 | Meynell . |
| 4,131,130 | 12/1978 | Ruby . |
| 4,253,480 | 3/1981 | Kessel ...................... 137/487.5 X |
| 4,395,258 | 7/1983 | Wang et al. . |
| 4,462,428 | 7/1984 | Guenther et al. . |
| 4,706,687 | 11/1987 | Rogers et al. . |
| 4,715,396 | 12/1987 | Fox . |
| 4,747,424 | 5/1988 | Chapman ................... 137/596.17 X |
| 4,836,234 | 6/1989 | Hicks . |

*Primary Examiner*—Alan Cohan
*Attorney, Agent, or Firm*—Barry L. Copeland; Jeffrey S. Schira

[57] ABSTRACT

A pressure control system is disclosed for closely regulating the pressure level of a controlled volume. The system comprises first and second sources, a throttled valve for controlling the flow rate of the fluid between each of the first and second pressure sources and the controlled volume, and a feedback control. The throttled valve comprises a rotationally mounted cam, a housing for receiving the cam and including a chamber, a first port coupled to the first pressure source, a second port coupled to the controlled volume, and a third port coupled to the second pressure source. The cam has first and second cam surface portions for defining corresponding first and second transfer functions of fluid flow through the first and second ports, respectively. First and second metering needles are associated with the first and third ports respectively for throttling the fluid flows therethrough. The first and second metering needles are disposed to engage respectively the first and second cam surface portions. A transducer is associated with the controlled volume for providing an output signal indicative of the pressure level therein. A set point indicative of the desired pressure level within the controlled volume is entered into the feedback control, which compares the entered set point with the measured pressure level to determine that desired angular position of the cam with respect to the housing which will provide a corresponding desired rate of fluid flow through the first and second ports.

18 Claims, 3 Drawing Sheets

PROPORTIONAL VALVE AND PRESSURE CONTROL SYSTEM

FIELD OF THE INVENTION

This invention relates generally to apparatus for controlling the pressure and/or vacuum level within a controlled volume and, more particularly, to a valve disposed intermediate a pressure/vacuum supply and the controlled volume for proportionately and smoothly controlling the rate of fluid flow therebetween. One illustrative embodiment of this invention has particular application for use in ophthalmic surgery for automatically regulating and controlling the vacuum level in a debris receptacle for suctioning unwanted materials such as vitreous from the interior of the human eye.

BACKGROUND OF THE INVENTION

In many applications including ophthalmic surgery, it is necessary to closely and proportionately regulate the pressure (including negative pressure or vacuum) of a controlled volume such as the debris receptacle, which is connected to a probe or cannula used in ophthalmic surgery. Such instruments draw eye tissue into the cutting ridges by the use of suction. Tissue removal rate is directly related to the level of negative pressure or vacuum applied to the instrument. Thus, controlling the negative pressure or vacuum level to a fine degree is an absolute necessity to provide the surgeon a like degree of control of tissue removal. Loss of pressure or vacuum control will result in damage to the eye, e.g. withdrawing or suctioning of unwanted material from the eye's interior. In ophthalmic surgery, the surgeon needs the capability of rapidly decreasing or eliminating the vacuum. A vivid example of this need arises when the surgeon may inadvertently start to cut and suction a part of the eye retina into the surgical instrument. At that instant, the surgeon must immediately remove the vacuum from the probe.

Pressure/vacuum control systems employed in ophthalmic surgery generally include a source of negative pressure or vacuum coupled to the controlled volume or debris receptacle, a fluid control valve disposed therebetween and a surgical instrument connected to the debris receptacle. U.S. Pat. Nos. 4,395,258 and 4,706,687 are illustrative of such prior art systems and both disclose the use of solenoid type valves, which are electrically controlled to be fully opened or fully closed. These systems include a pressure sensor coupled to the debris receptacle for measuring the pressure therein and a feedback type of control system, which responds to a negative pressure less than a preset limit, to open its solenoid valve, whereby the vacuum or negative pressure within the debris receptacle may be increased. A feedback signal is applied to actuate the solenoid valve, which immediately opens to interconnect the debris receptacle to the vacuum source, whereby the pressure within the debris receptacle is immediately reduced.

The system disclosed in U.S. Pat. No. 4,395,258 also includes a second solenoid type valve interconnected between the debris receptacle and atmospheric pressure. In typical operation, each solenoid valve is totally opened or closed. If the vacuum within the debris receptacle is found to be too high, the second valve connected to atmospheric pressure is opened, whereas the first valve remains closed. Oppositely, if the vacuum is determined to be too low, the first valve is opened and the second atmospheric valve is closed. More specifically, these solenoid valves are operated in a pulse modulation (PM) or bang-bang mode whereby the fluid flow therethrough is regulated. In particular, the valve signal is turned on and off so that the duty ratio of off to on permits the desired fluid flow rate. When turned on, the valve signal is applied to the solenoid valve which moves towards its open position to permit fluid flow therethrough and when off, the valve signal is removed from the valve which returns towards its closed position, typically with the aid of a spring bias. Thus, the solenoid valve is rapidly moved between its open and close positions. There are several disadvantages to the use of such solenoid valves and of operating them in a PM mode. First, such valves are relatively noisy. Solenoid valves tend to wear out relatively quickly in that the valve is opening and closing rapidly; the valve seats are repeatedly struck and tend to wear out under repeated impact. Also, such solenoid valves operated in a PM mode tend to respond relatively slowly to a desired change in fluid level, requiring as much as 1–2 seconds to adjust from a first steady state condition for a first fluid flow to a second steady state condition for a second, different fluid flow. Further, the continuous opening and closing of such solenoid valves tends to impart pulsations to the fluid whose pressure level is being regulated. When it is desired to increase the speed with which a pressure change is made, it is necessary to employ a larger solenoid valve having a larger opening and valve mechanism. Though speed may be increased by a larger solenoid valve, larger solenoid valves tend to impart even greater pressure perturbations to the regulated fluid.

SUMMARY OF THE INVENTION

It is an object of this invention to provide a new and improved pressure/vacuum control system, wherein changes of pressure are accurately and proportionately effected.

It is a further object of this invention to provide a new and improved valve, which may be accurately controlled to proportionately change the fluid flow therethrough.

It is a still further object of this invention to closely control the rate of fluid flow by selectively setting a fluid valve to a partially open or throttled position.

In accordance with these and other objects, this invention relates to a throttled valve for selectively controlling the flow rate of a fluid between at least one pressure source and a controlled volume, whereby the pressure level within the controlled volume is closely regulated. The throttled valve comprises a housing including a chamber and first and second ports both coupled to the chamber and adapted for communication respectively with the pressure source and the controlled volume. A valve mechanism is associated with the first port and is disposable continuously to a selected position between a closed state and an open state, whereby the fluid flow rate through the first port is set in accordance with the selected position. An actuation mechanism is operatively coupled to the valve mechanism for selectively disposing the valve mechanism to its selected position to throttle the fluid flow through the first port, whereby the rate of the throttled fluid flow is set and the pressure level within the controlled volume is regulated accordingly.

In an illustrative embodiment, the actuation mechanism includes a cam, Which has at least one cam surface portion of a configuration for defining a transfer function of the fluid flow rate. The valve mechanism may include a spring biased needle, which is disposed within the first port to throttle fluid flow therethrough and disposed to engage the cam surface portion, whereby the fluid flow rate through the first port and thus the pressure level within the controlled volume are regulated in accordance with a selected position of the cam.

In a further aspect of this invention the throttled valve further includes a third port coupled to the chamber and a second pressure source. A second metering needle is disposed within the third port for throttling the fluid flow between the second pressure source and the controlled volume. The cam includes a second cam surface portion of a configuration for defining a second transfer function of the fluid flow rate different from the first mentioned transfer function to regulate the fluid flow through the third port.

In a further aspect of this invention, the throttled valve includes a stop for limiting the movement of the cam to define a calibration point on the cam surface portion. The calibration point defines a particular angular position of the cam and a corresponding position of the metering needle with respect to the first port to determine a corresponding fluid flow rate through the first port. Illustratively, the corresponding flow rate is the maximum fluid flow rate through the first port.

In a still further aspect of this invention, the throttled valve is incorporated into a pressure control system for closely regulating the pressure level of the controlled volume. The pressure control system includes a transducer or sensor coupled to the controlled volume for providing an output signal indicative of the pressure level therein. A set point indicative of the desired pressure level within the controlled volume is entered into a feedback control, which compares the set point with the measured pressure level to provide a difference or error signal indicative of that desired position of the cam that will provide a corresponding desired rate of fluid flow through the first port.

The position signal is applied to a drive motor, which moves the cam to the desired position, whereby the desired fluid flow rate through the first port is established and the desired pressure level within the controlled volume is determined. The drive motor may be a stepping motor, which responds to the output position signal to be driven in a selected direction and responsive to each of a series of pulses to be moved a given, discrete distance. The feedback control determines the difference between the entered set point and the measured signal for predicting a count indicative of the extent which the cam needs to be moved to its selected position. The predicted count determines the number of pulses to be applied to the stepping motor.

DETAILED DESCRIPTION OF THE PREFERRED EMBODIMENTS

Figure 2:
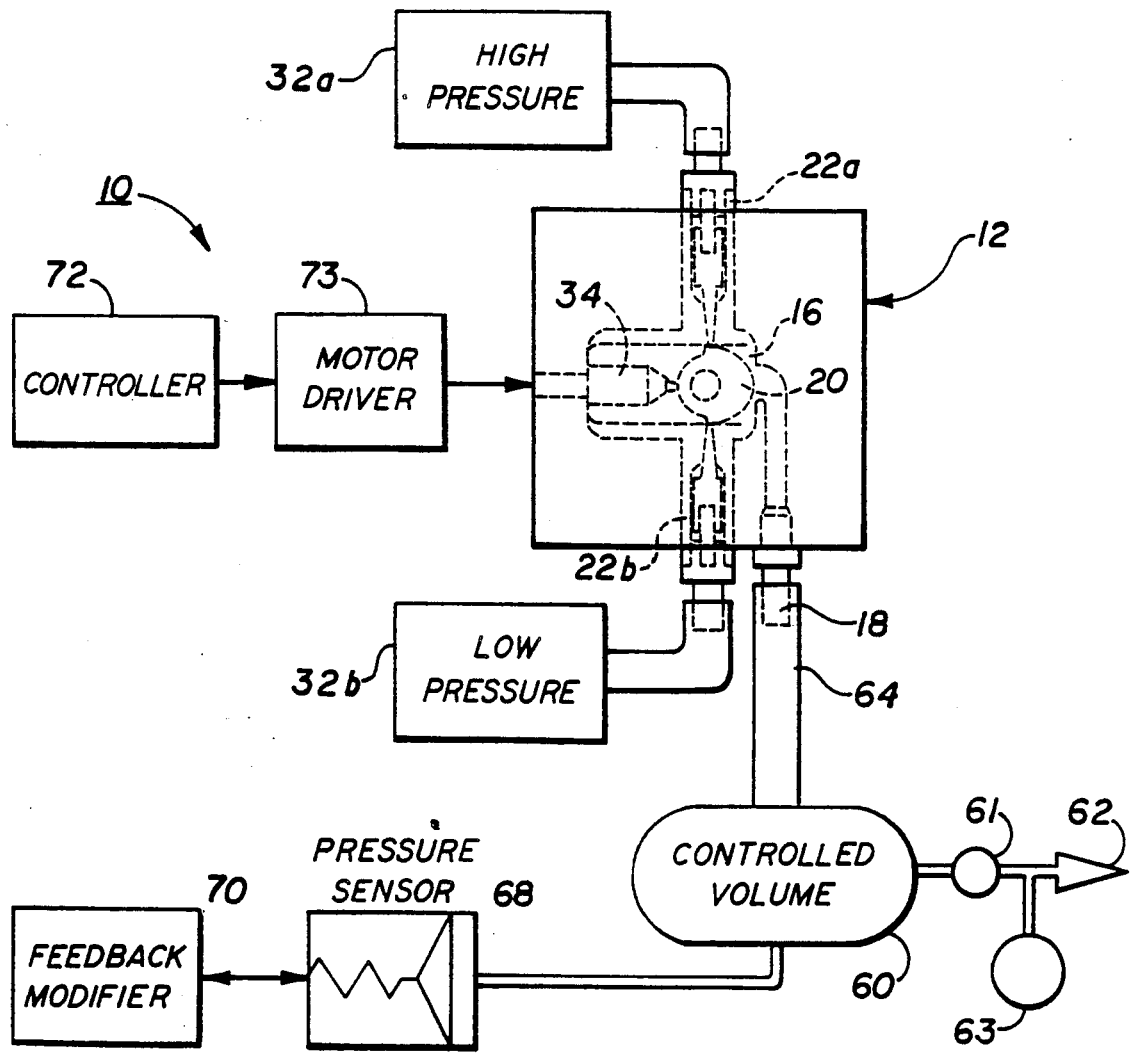
FIG. 2 is functional block diagram of the proportional valve and a feedback control system for sensing the pressure/vacuum of a controlled volume and for measuring and responding to the measure vacuum to responsively control the position of the valve's cam.

Referring now to the drawings and in particular to FIG. 2, there is shown a pressure control system 10 of this invention, which includes a proportional valve 12 for precisely and rapidly controlling the pressure level of a fluid such as gas within a controlled volume 60, and a feedback loop for regulating the proportional valve 12. The proportional valve 12 has a pair of input ports 22a and b respectively connected to a source 32a of positive pressure and a source 32b of negative pressure or vacuum. The ports 22a and b are in communication with a common chamber 16, which in turn communicates with a common or output port 18. That port 18 is in turn coupled by a conduit 64 to the controlled volume 60. When the system 10 of this invention is used in ophthalmic surgery, the controlled volume 60 is in turn connected to a surgical instrument 62 such an infusion/aspirator (I/A) hand piece or vitreous cutter. As described in greater detail by the co-pending, commonly assigned application entitled "Apparatus and Method for providing Continous Suction", filed on even date in the names of Hugh Jean Tyler et al., the controlled volume 60 is connected to the surgical instrument 62. In particular, there is described a plurality of valves which are illustrated by only a single pinch type valve 61, which may be closed at the direction of the surgeon in emergency situations, e.g. when an undesired portion of tissue is being sucked into the instrument 62. In addition, a debris container 63 is coupled to the surgical instrument 62, whereby cut tissue may be sucked away into the container 63. As described in the co-pending application, the container 63 may be removed from the pressure control system 10 and discarded.

The term "fluid" is used herein in its normal sense to canote either a gas or a liquid. It is contemplated that this invention is applicable to the control of the pressure of either a gas or a liquid. This invention would have application to the flow rate control of well known hydraulic fluids.

Figure 1B:
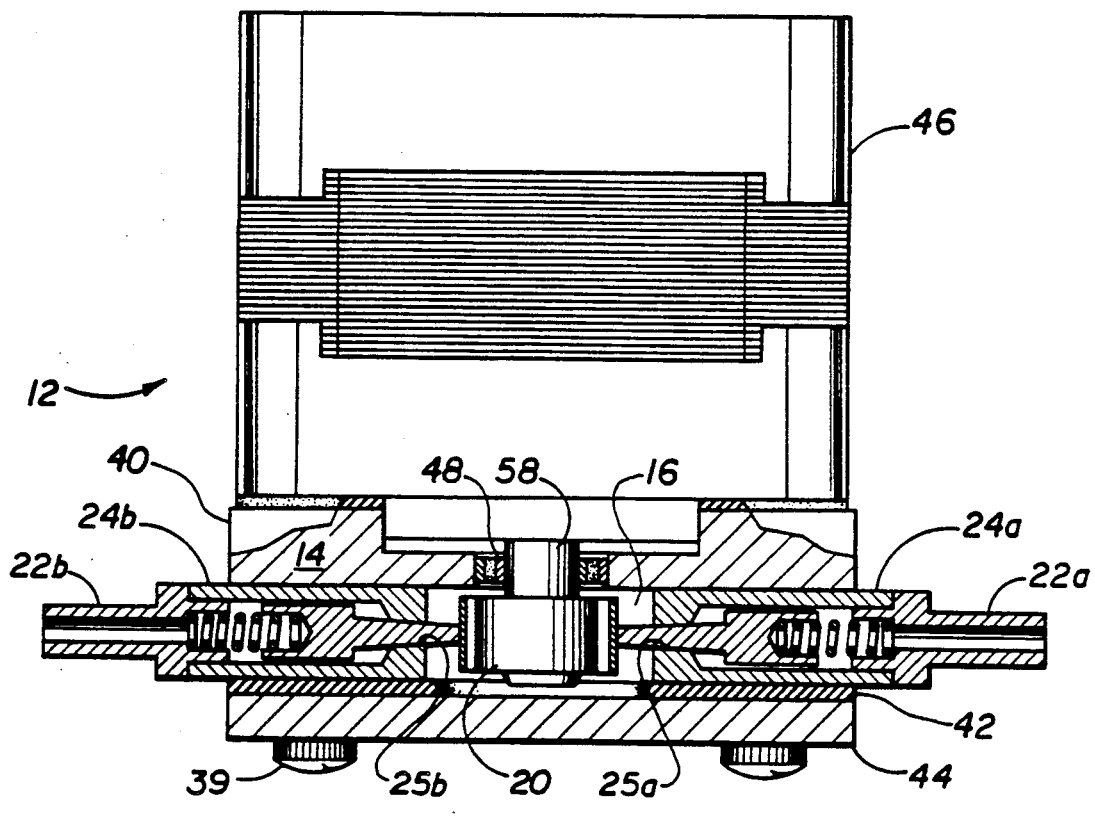
FIG. 1B is a top, plan view of the proportional valve shown in FIG. 1A and its stepper motor for selectively and controllably disposing the cam of the proportional valve to a desired position.
Figure 1A:
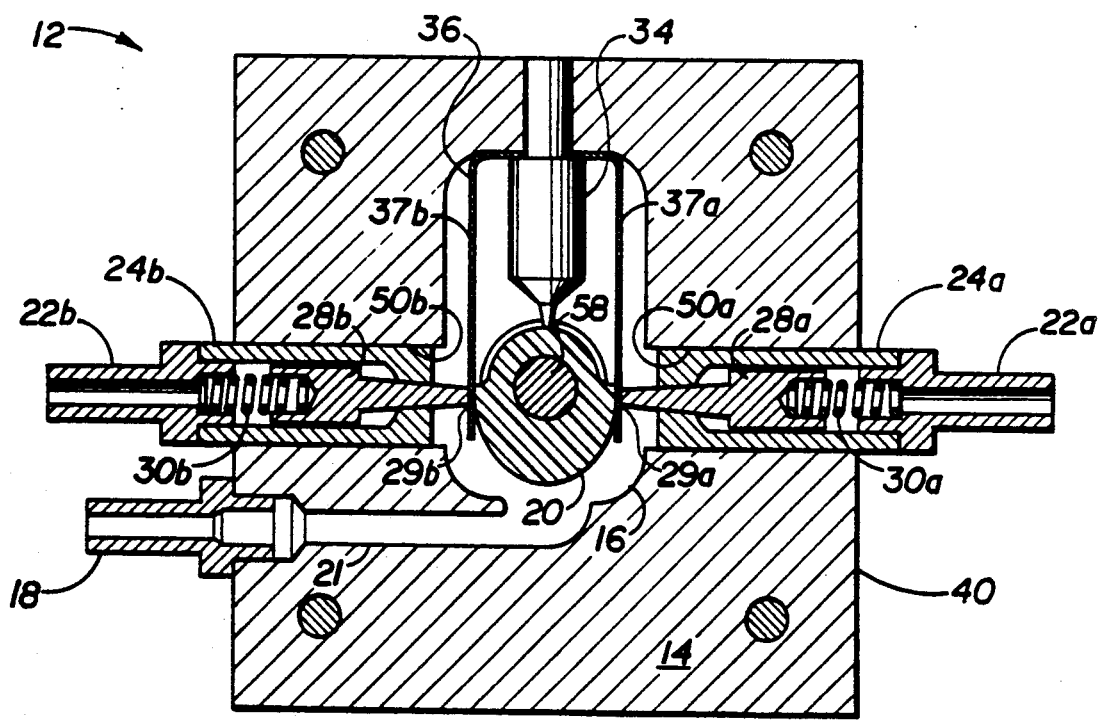
FIG. 1A is a front view of a proportional valve, with its cover removed, in accordance with the teachings of this invention.

As it will be explained in detail below, the proportional valve 12 selectively couples pressure from either the positive pressure source 32a or the negative pressure source 32b (but not both) to the controlled volume 60 via the common chamber 16, the common port 18 and the conduit 64. The proportional valve 12 included a cam 20, which is rotatively driven by a stepping motion (see FIG. 1B) via a drive shaft 58 to a desired angular position. As will be explained, the cam 20 may selectively connect one of the pressure sources 32a and b or, in its rest position as shown in FIG. 1A, may disconnect both pressure sources 32a and b from the controlled volume 60. Further, the cam 20 controls the flow rate of fluid flow between one of the pressure sources 32a and b and the controlled volume 60, whereby the pressure level in the controlled volume 60 may be regulated.

The pressure or vacuum level within the controlled volume 60 is measured by a pressure sensor 68. The sensor 68 is in communication via a conduit 66 with the controlled volume 60 to provide an analog output signal indicative of the pressure level therein. The output of the pressure sensor 68 is applied to a feedback modifier 70, which performs two essential functions: the first to amplify the signal in an illustrative range of 10-20 mv to a level suitable to be used by a digital microprocessor, e.g., 5 v, and the second to convert that amplified signal from analog to digital form to be applied to the controller 72. The controller 72 may take the form of a programmed microprocessor such as that model 6800 manufactured by Motorola. The operator, a surgeon where this pressure control system 10 is used in surgical procedures, sets a selected control or set point via a suitable input device, which is connected to the controller 72. The microprocessor is programmed to compare the measured value of the pressure level within the controlled volume 60 with the operator entered set point. In one illustrative embodiment of this invention, the microprocessor is programmed with a predictive control scheme to determine the desired angular position of the cam 20 and the direction in which a stepping motor 46 (see FIG. 1B) needs to be driven to dispose its cam 20 at the desired position to regulate the control pressure level within the volume 60. The controller output is applied to a motor driver 73, which acts as a power amplifier to amplify and apply the control signals to the stepping motor 46. The motor driver 73 may take the form of that integrated circuit manufactured by Motorola under its part no. 3479. In an illustrative embodiment of this invention, the stepping motor 46 may take the form of that 2-phase Vexta stepping motor manufactured by the Oriental Motor Company, Ltd. under its model no. PXC43-03AA.

Referring now to FIGS. 1A, B and C, the detailed structure of the proportional valve 12 will now be explained. The proportional valve 12 includes a housing 14 comprised primarily of a main body 40 in which the common chamber 16 is formed and a cover 44 connected to the main body 40 by fasting means such as a plurality of bolts 39. As shown in FIG. 1B, a gasket 42 is inserted between the cover 44 and the main body 40, whereby a pneumatic seal is formed about the common chamber 16. Further, as particularly shown in FIG. 1A, a pair of body openings 50a and b are formed within the main body 40 in communication with and extending from the common chamber 16 in opposite directions to the first and third ports 20a and b, respectively. A conduit 21 is also formed within the main body 40 interconnecting the common chamber 16 and a second or common port 18. Cylindrically shaped valve bodies 24a and b are respectively disposed within the body openings 50a and b in a tight fitting relationship therewith. Metering needles 28a and b are respectively disposed within the valve bodies 24a and b such that their tapered ends are disposed toward and engage the cam 20 as shown in FIGS. 1A and B. The cylindrically shaped ports 20a and b are fitted within the open ends of the valve bodies 24a and b to compress respectively the biasing springs 30a and b between its port 22 and its metering needle 28, whereby the needle 28 is spring biased toward the cam 20. The valve bodies 24, their metering needles 28 and bias springs 30 form a valve mechanism continuously disposable to a selected position between a closed state, e.g., where as shown in FIG. 1A the tapered end of the needle 28 completely blocks the opening 25 of its valve body 24, and an open state, e.g., where the needle 28 is withdrawn from the opening 25. Such a valve mechanism is proportional in that its needle 28 is disposable to any selected position in a continuum between its open and closed states to throttle the fluid flow and to regulate the rate of fluid flow dependent upon the selected needle position.

A cam follower 36 is disposed within the common chamber 16 and is of a generally U-shaped configuration having a pair of legs 37a and b extending downwardly as shown in FIG. 1A to engage the opposite sides of the cam 20. The cam follower 36 is made of a flexible material such as stainless steel and its legs 37a and b act as springs to exert a force against the opposite sides of the cam 20. As will be explained, the distal, pointed ends 29a and b of the needles 28a and b are biased by their respective springs 30a and b to engage respectively the legs 37a and b, whereby the relative position of the metering needle 28 with respect to its valve body 24 is dependant upon the angular position of the cam 20. The spring constants of the biasing springs 30a and b are set as a function of the maximum negative pressure or vacuum within the vacuum source 32b so that the biasing spring 30 will retain the metering needle 28 in its closed position with respect to its valve opening 25, i.e., the force exerted by the biasing spring 30 is greater than that exerted by the negative pressure or vacuum source 32b. Each of the valve bodies 24a and b has an opening 29 in that end disposed toward the cam 20. Each of the metering needles 28 is tapered toward its end 29 as shown in FIGS. 1A and B. As the cam 20 pushes against one of the metering needles 28, it is moved linearly away from its opening 25 to thereby increase the fluid flow between one of the pressure sources 32a and b and the controlled volume 60 via the common chamber 16, the common port 18 and the conduit 64.

When it is desired to change the pressure level within the controlled volume 60, one of the metering needles 28 is actuated, i.e., is moved by the cam 20 and its associated leg 37 of the cam follower 36 to be displaced from its opening 25, whereby a fluid flow occurs between the pressure source 32 and the controlled volume 60. The rate of that flow is dependant upon the size of the opening or space between the metering needle 28 and the openings 25 of the valve bodies 24. The flow rate between the common chamber 16 and the controlled volume 60 is a function of the geometry of a cam surface 76 of the cam 20 (best shown in FIG. 1C), the geometry of the metering needle 28, the fluid characteristics, and the displacement of the needle valve 28 with respect to their valve openings 25. As explained above, the displacement of the metering needle 28 along its axis is a function of the angular position of the cam 20. As shown in FIG. 1B, the angular position of the cam 20 with respect to its metering needles 28a and b is set by the stepping motor 46, which is coupled to the cam 20 by a drive shaft 58. In order to maintain the pressure within the common chamber 16, a cam gasket 48 in the nature of a lip or gland seal is disposed about the drive shaft 58.

In an illustrative embodiment of this invention, the cam 20 forms an actuation mechanism for disposing the needle 28 to its selected position. Though the cam 20 is shown as being rotatively mounted and driven by the stepping motor 46, a cam could be linearly driven so that its cam surface engages and displaces the needle 28. In a broader context, the cam could be replaced by a solenoid type of actuation mechanism having a coil, which is energized electrically to a degree that the needle is disposed to its selected position between closed and open (maximum) states and the fluid flow rate is regulated to a like degree.

In that illustrative embodiment shown in FIGS. 1A and B, the metering needles 28 have a straight, conical configuration tapering toward their ends 29a and b. Though the needle configuration is linear, the fluid flow rate is a function of the area between the metering needle 25 and the interior surface of the valve bodies 24a and b. Thus, the flow rate varies as the square of the linear displacement of the metering needle 25. The flow rate through the ports 20a and b can be varied by changing the configuration of the metering needles 25; for example, the flow rate may be made a linear function of needle displacement by making the configuration of the metering needle 25 of an "ogive" shape.

Figure 1C:
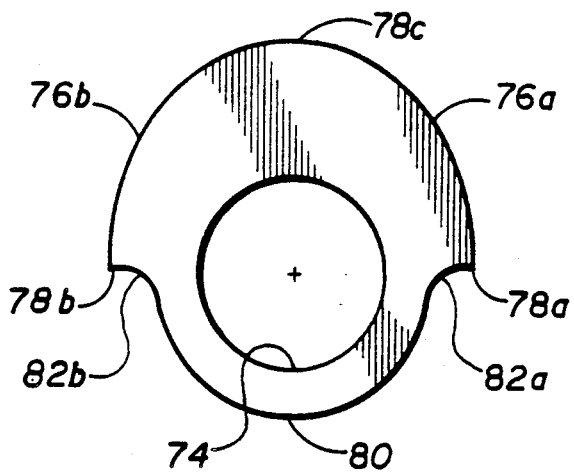
FIG. 1C is an enlarged view of the valve's cam, particularly illustrating the cam surface thereof for selectively imparting a proportionate opening and closing of the valve's ports.

In one illustrative embodiment of this invention as most clearly shown in FIG. 1C, the cam surface 76 has two symmetrical portions 76a and b. Each of the cam surface portions 76a and b has a point 78a or b of minimal radius. The radius of the surface linearly increases as a function of angular rotation to a point 78c of maximum radius. Such cam surfaces 76a and b are generated in accordance with an Archimedes spiral to provide an "ogive" configuration. Thus, as the step motor 46 rotates the cam in either direction from that rest position shown in FIG. 1A, the metering needles 28a and b are displaced linearly as a function of cam rotation.

When the cam 20 is disposed in its rest position as shown in FIG. 1A, the ends 29a and b of the metering needles are displaced a minimum clearance from the respective legs 37a and b of the cam follower 36, whereby it is assured that the metering needles 28a and b fully close the valve opening 25a and b of their valve bodies 24. The minimum clearance is set as a function of the temperature coefficient of the material of which the needles 28 is made to insure that the ends 29a and b of the metering needles 28 will not expand to engage their respective legs 37 for a contemplated change of temperature.

The cam follower 36 and its leg 37a and b are used to eliminate the friction that would otherwise be exerted by the rotating cam 20 and its cam surface 36 on the ends 29a and b of the metering needles 28a and b, respectively. Such friction could assert a twisting force along a line perpendicular to the needle axis, which could otherwise retard the ready opening and closing of the metering needles 28. In addition, without the cam follower 36, the point of application of force provided by the cam surface 36 would vary as a function of the angular position of the cam 20, i.e., a tangent disposed on the cam surface 76 at the point of needle contact would be disposed at a varying angle with respect to the surface defined by the ends 29a and b of the metering needles 28, as a function of cam position The use of the cam follower 36 insures a substantially constant relation between its legs 37 and the needle ends 29 and that the opening and closing of the metering needles 28 is made as uniform as possible, regardless of cam position.

Referring particularly to FIGS. 1B and C, the cam 20 also has a recessed portion 80 extending about its circumference for approximately 180° and terminating respectively on either end by limit surfaces 82a and b. As shown in FIG. 1A, a cam stop 34 is affixed within the common chamber 16 to engage either of the limits surfaces 82a and b to prevent further rotation of the cam 20 by its stepping motor 46. The placement of the limits surfaces 32a and b determines a particular point on the cam surface 76, e.g., the point 78c of maximum radius. Thus, when the setting motor 46 has rotated the cam 20 in either direction so that the cam stop 34 engages either of the limits surfaces 82a or b, it is known that the point 78c of maximum radius is disposed to engage one of the metering needles 28a and b, whereby that corresponding valve opening 25 is fully opened and a maximum fluid flow is established through that port 22. The cam stop 34 also serves to ensure that the cam surface portion 76a only engages the end 29a of the metering needle 28a and that the cam surface portion 76b only engages the end 29b of the metering needle 28b. Further, as will be explained, the cam stop 34 provides a mechanism for calibrating the control of the step motor 46.

Each energizing pulse cause the stepping motor 46 to rotate its drive shaft 58 and therefore the cam 20 a uniform, discrete angle of rotation in incremental or step fashion. Thus, the number of steps between the rest position as shown in FIG. 1A and that position at which the point 78c of maximum radius is disposed to abut either of the metering needles 28a and b, may be determined. In an illustrative embodiment of this invention, the cam 20 has a minimum radius of 0.197 inches and a maximum radius of 0.251 inches. Further, the cam 20 may be rotated through an angle of 85° from either of the points 78a or b in 94 discrete steps to dispose the cam 20 so that its point 78c of maximum radius is disposed adjacent one of the metering needles 28.

Though a symmetric cam 20 with cam surface portions 76a and b of equal extent has been shown, it is appreciated that the cam profile may be modified to provide more precise control in a particular range of rotation. For example, the cam surfaces could be made asymmetrical; one cam surface portion would be dedicated to the actuation of one metering needle and would be made longer than a second cam surface portion. A cam could be provided with but a single surface for controlling the fluid flow from but a single pressure source to the controlled volume. In the illustrative embodiment described above with regard to FIGS. 1A, B and C wherein there is a dead band disposed intermediate the two cam surfaces, i.e., both valves are closed when the cam 20 is disposed at its rest position. That dead band between the cam surface portions could be eliminated. In other words, there would be a small portion of the cam rotation in which both metering needles 28a and b would be actuated and the fluids would flow through the common chamber 16 from both sources 32a and b. The result of such a cam surface configuration would be to provide a continuous smooth transfer function as the cam is rotated.

In an illustrative embodiment as shown in FIGS. 1A and 2, a positive pressure source 32a of 10 psig is connected to the first port 22a and a second negative pressure source 32b is coupled to the third port 22b, whereby the pressure within the controlled volume 60 may be regulated at pressure levels below atmospheric pressure, at pressures above atmospheric pressure or at atmospheric pressure. As show in FIG. 1A, if the controller 72 is set to establish a positive pressure with regard to atmospheric, the stepping motor 46 is controlled to drive the cam 20 in a counter clockwise direction from that rest position shown in FIG. 1A to the desired cam position, whereby the third port 22b is closed and the first port 22a in communication with the positive pressure source 32a is throttled to that degree set by the cam position so that a corresponding positive pressure level is set within the controlled volume 60. Conversely, if a negative pressure set point is set into the controller 72, the cam 20 is rotated clockwise from that position shown in FIG. 1A, whereby the first port 22a is closed and the third port 22b is opened so that the negative or vacuum pressure source 32b is coupled to the control volume 60 and a vacuum is established therein. Though positive and negative pressure sources are described in an illustrative embodiment of this invention, it will be appreciated that the pressure control system 10 of this invention could be operated with a single pressure source coupled to the third port 22b while the first port 22a is connect to atmospheric pressure. The use of a positive pressure source 32a is desired to clear the surgical instrument 62 by forcing fluid therethrough to remove tissue particles from its opening.

Figure 3:
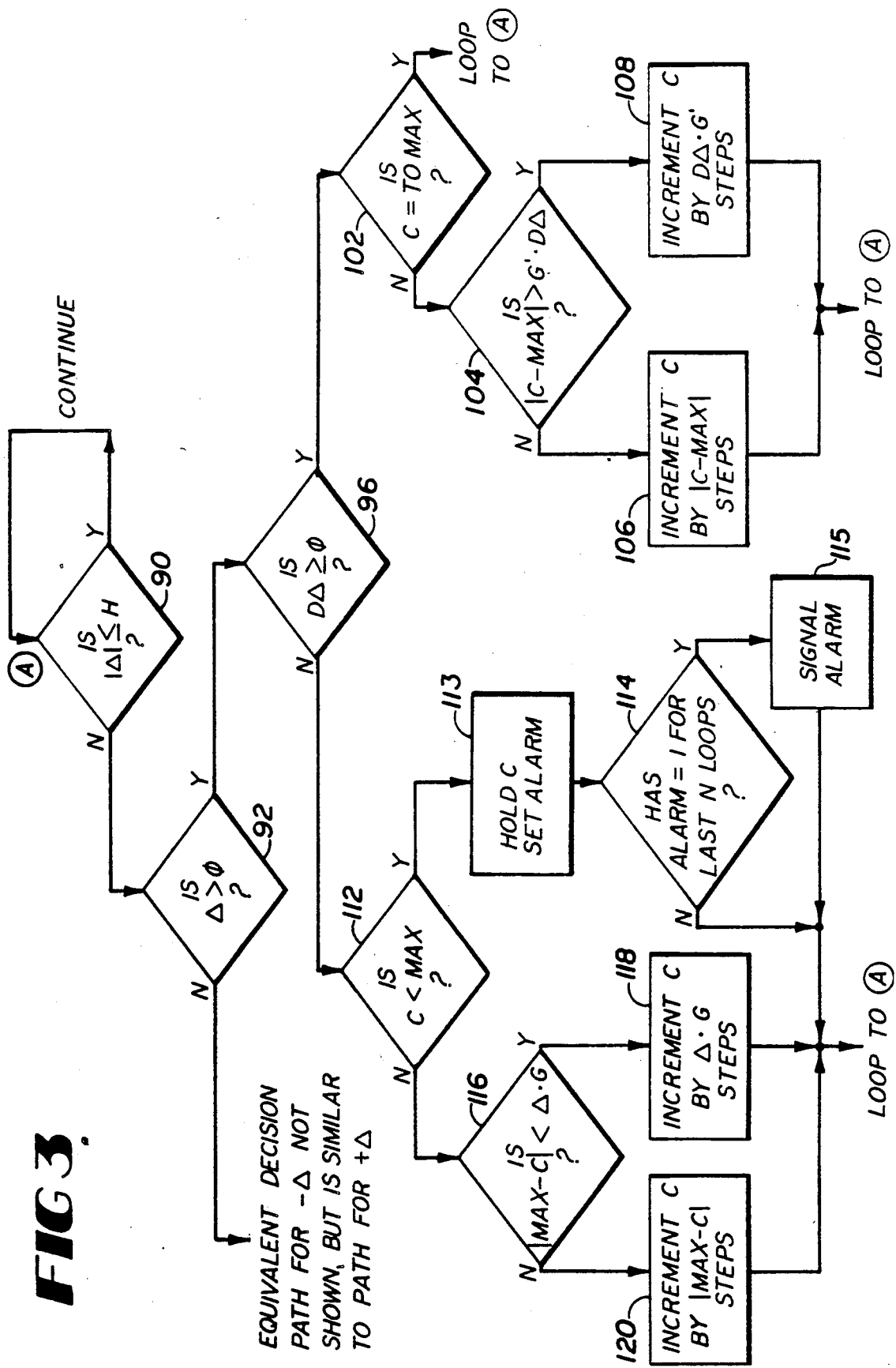
FIG. 3 is a flow diagram of the program to be executed by microprocesssor incorporated into the controller of the feedback control shown in FIG. 2.

The microprocessor incorporated into the controller 72 of the feedback control, as shown in FIG. 2, is programmed in accordance with that program illustrated by the flow diagram of FIG. 3. Initially in step 90, the difference Δ is determined as the difference between the set point indicative of the desired pressure level within the controlled volume 60 and the measured value, which is provided by the output signal of the pressure sensor 68. Then, step 90 determines whether the absolute value of that difference Δ is less than or equal to a histerysis value H. In other words, is the difference Δ greater than a predetermined minimum as indicated by the value H, which may be disregarded in this control scheme? If the difference Δ is less than or equal to H, no control action is taken and, as indicated in FIG. 3, the control loop returns to point A in preparation for the next program loop. In this system, inputs are derived from the pressure sensor 68 indicative of the measured pressure level within the controlled volume 60 and the set point entered by the operator of this system, e.g., a surgeon. In an illustrative embodiment of this invention, the inputs to the controller 72 may be poled repetitively, the program loop or control period being in the order of 1-10 milliseconds.

Continuing the description of the flow diagram of FIG. 3, if the difference Δ is greater than the histerysis factor H, step 92 determines whether that difference Δ is greater than zero or not. It is understood that the pressure level may have positive and negative (vacuum) values. If the measured value is greater than the set point, negative values of Δ will result. Step 92 permits both positive and negative values of Δ to be processed. The remaining steps of the control program shown in FIG. 3, operate on positive values of Δ, it being understood that an identical set of programmed steps are included to process negative values of Δ. Next for positive values of the difference Δ, the first derivative of the difference DΔ is taken and step 96 determines whether DΔ is greater than or equal to zero. In other words, is the difference Δ getting larger (yes) or smaller (no). If Δ is becoming larger, the program moves to step 102. As will become evident from the following discussion, step 96 separates the control process into a derivative scheme operating on DΔ which is implemented by steps 102 to 108, and a proportional scheme operating on Δ which is implemented by steps 112-120.

Step 102 examines a control setting C. The control setting C is the determined angular position of the cam 20 as measured in terms of the number of steps from that rest position of the cam 20 shown in FIG. 1A and corresponding to the number of pulses needed to drive the stepping motor 46 to that position. In particular, step 102 determines whether the present control setting C is at its maximum setting MAX corresponding to that position of the cam 20 when its point 78 of maximum radius is disposed to abut the metering needle 29 of either of the ports 20a and b. If at its maximum position as decided in step 102, the program returns to point A at step 90. If at some intermediate position, the program moves to step 104, which determines the difference between the control setting C and the maximum setting MAX of the cam 20, which is likewise expressed as a number of steps. In other words, step 104 determines how much further the cam 20 may be rotated to its maximum position corresponding to point 78c, i.e., how many pulses are required to drive the stepping motor 46 to rotate the cam 20 to its maximum position. If the absolute value of that difference is determined by step 104 to be greater than the product of a selected derivative gain constant G' and DΔ, the value of the control setting C is incremented in step 108 by a number of steps equal to the product of DΔ*G'. As its name implies, the derivative gain constant operates on DΔ and its value is variably set depending upon the desired operation of the feedback control. If response speed is desired in contrast to control stability, a high value of the gain factor G' is selected. If stability is desired at the expense of response speed, a lower value of control constant G' is set. Selecting higher values of the control constant G' affects the control of the cam position, i.e., the cam 20 tends to oscillate about the predicted cam position before coming to rest at that predicted position. If the difference of the control factor C and its maximum value is less than the product DΔ*G', the control setting C is incremented in step 106 by that number of steps equal to the difference of the control setting C and its maximum value MAX. The controller 22 applied a number of pulses equal to the number of the incremented or decremented steps via the motor driver 73 to the stepping motor 46, whereby the cam 20 is rotated to its selected position according to the new control setting C. Illustratively, the processor 72 applies the "incremented" or "decremented" number of pulses during the present program loop or control period. After either step 108 or 106 is completed, the control returns to point A to re-execute step 90.

If the difference Δ is growing smaller as decided by step 96, the program moves to step 112 to determine whether the control setting C is disposed at its maximum value MAX, i.e., whether the cam 20 is disposed at its maximum position 78c. If at its maximum position, the program moves to step 113, which holds the cam 20 at its maximum position and sets a flag within the microprocessor to indicate a potential alarm condition. If the control loops back through step 113 for a predetermined number N of periods, e.g., 10, as determined by step 114, a signal alarm is actuated by step 115, whereby the operator is warned that the cam 20 is at its maximum position and the feedback control is no longer functioning to regulate the pressure within the controlled volume 60. After the alarm, the control loop returns to point A at step 90.

If the control setting C is not at its maximum value MAX as determined in step 112, the program moves to step 116, which compares the absolute value of the difference between the control setting C and its maximum value MAX with the product of the difference Δ and a proportional control constant G. As its name implies, the proportional gain constant G operates on values of the difference Δ and is set on a principal similar to that used to set the derivative gain constant G'. Using separate constants G and G' permits a finer control of the control setting C. If |MAX-C| is greater than Δ*G, the control setting C is incremented by that number of steps equal to the product Δ*G, whereby the number of pulses corresponding to that product Δ*G is sent to the stepping motor 46 which rotates the cam 20 to displace the metering needle 25 so that a corresponding flow rate is established through its port 20. Whether the flow rate is incressed or decressed depends on whether the constants G or G' have been assigned positive or negative values. After incrementing the control setting C, the control program returns to point A at step 90. However, if the difference between the control setting C and its maximum value MAX is less than the product Δ*G, the value of the control setting C is incremented by a number of steps corresponding to the absolute value of the difference of the control setting C and its maximum value MAX. Thus, when the control setting C indicative of the position of the cam 20 is disposed almost at its maximum value as indicated by the step 116, a lesser number of steps is applied to the stepping motor 46 than when the cam 20 is disposed closer to that rest position as shown in FIG. 1A. After either step 120 or 118, the control program returns to point A at step 90.

Thus if the values of Δ are positive as determined by step 92, the control setting C indicative of the angular position of the cam 20 is incremented as explained above with respect to steps 96-120, tending to rotate the cam 20 towards its MAX position and to open the ports 22a or b. On the other hand, if Δ is found in step 92 to have negative values, the control moves to that equivalent decision path referred to but not shown in FIG. 3, whereby the control setting C is decremented and the ports 22 are closed to decrease the flow rate between one of the pressure sources 32a or b and the control volume 60. It is appreciated that the ports will be closed when the cam position and thus the port overrun the predicted selected position and control needs to be trimmed While the invention has been shown and described in detail, it is apparent that this invention is not to be considered as being limited to the exact form disclosed, and that changes in detail and construction may be made therein within the scope of the invention, without departing from the spirit thereof. For example, though this invention has been described in the context of ophthalmic surgery, it has application to other arts where the close regulated control of a fluid flow rate is needed.

What is claimed is:

1. A pressure control system for closely regulating the pressure level of a controlled volume, said system comprising:
    a) a first pressure source and a second pressure source;
    b) a throttled valve comprising a housing including a chamber, a first port couple to said first pressure source, a second port coupled to said controlled volume, a third port opposite said first port and coupled to said second pressure source, a first valve means associated with said first port and a second valve means associated with said third port and disposable continuously to selected positions between a closed state and an open state to set that rate of fluid flow through said first port and said third port in accordance with said selected positions of said first and second valve means, and actuation means operatively coupled to said first and second valve means for selectively disposing said first and second valve means at said selected positions to throttled fluid flow through said first port and said third port;
    c) transducer means associated with the controlled volume for providing a selected position output signal indicative of a pressure level therein;
    d) control means for receiving a set point indicative of the pressure level within the controlled volume and for comparing said set point with said selected position output signal to provide a signal indicative of said selected positions of said first and second valve means that will provide the corresponding desired rate of fluid flow through said first port and said third port; and
    e) said actuation means comprises a cam rotatably mounted within the chamber so as to actuate the first and second valve means and having a first cam surface portion and a second cam surface portion of a configuration for defining a first transfer function of the rate of fluid flow through said first port and said third port and responsive to said selected position output signal for disposing said first and second valve means to said selected positions, and a cam follower mounted within the chamber having a first flexible arm with a first inside surface and a first outside surface and a second flexible arm with a second inside surface and a second outside surface, the first flexible arm being spring biased such that the first inside surface is disposed against the first cam surface and the first outside surface is disposed against the first valve means, the second flexible arm being spring biased such that the second inside surface is disposed against the second cam surface and the second outside surface is disposed against the second valve means, whereby the pressure level within the controlled volume is regulated accordingly.

2. The pressure control system as claimed in claim 1, wherein said first pressure source is of a first pressure level, and the second pressure source is of a second pressure level differing from said first pressure level.

3. The pressure control system as claimed in claim 2, wherein said second cam surface portion is of a configuration for defining a second transfer function of the fluid flow rate through the third port different from said first transfer function.

4. The control system as claimed in claim 3, wherein there is further included stop means for limiting the movement of said cam, whereby said first mentioned cam surface portion engages only said first mentioned valve means and said second cam surface portion only engages said second valve means.

5. The control system as claimed in claim 4, wherein said stop means limits the movement of said cam in a first direction to define a first calibration point on said first mentioned cam surface portion and limits the movement of said cam in a second direction opposite to said first direction for defining a second point on said second cam surface portion, said first and second calibration points activate said first mentioned and second valve means to effect a maximum fluid flow rate through their respective first mentioned and third ports.

6. The pressure control system as claimed in claim 1, wherein said selected position output signal provides an indication of the direction in which said cam is to be moved and a series of pulses, said actuation means further comprising a stepping motor and responsive to said selected position output signal to move said cam in said given direction and responsive to each of said pulses to move said cam a discrete distance.

7. The pressure control system as claimed in claim 6, wherein said selected position output signal of is an analog signal, and said control means further includes means for receiving and converting said analog desired position output signal to a digital signal, and means for determining the difference between said set point and said digital signal for predicting a count indicative of the extent which said cam needs to be moved to said selected position.

8. A throttled valve for selectively controlling the flow rate of a fluid between at least one pressure source and a controlled volume, whereby the pressure level within the controlled volume is closely regulated, said throttled valve comprising:
   a) a housing having a chamber;
   b) a first port in the housing in fluid communication with the chamber and adapted for communication with the pressure source;
   c) a second port in the housing in fluid communication with the chamber and adapted for communication with the controlled volume;
   d) a first needle valve associated with the first port and disposable continuously to selected positions between a closed state and an open state, whereby the fluid flow rate through the first port is set in accordance with said selected position of the needle valve;
   e) a cam rotatably mounted within the chamber on a shaft that penetrates the housing and having at least one cam surface portion of a configuration for defining a first transfer function of the rate of fluid flow through the first port and being mounted such that the cam surface portion actuates the first needle valve to disposed the first needle valve to its selected position;
   f) a spring for urging the needle valve into engagement with the cam surface; and
   g) a cam follower mounted within the chamber having at least one flexible arm with an inside surface and an outside surface, the flexible arm being spring biased such that the inside surface is disposed against the first cam surface and the outside surface is disposed against the first needle valve.

9. The throttled valve as claimed in claim 8, wherein there is further included a third port in the housing in fluid communication with the chamber and a second needle valve associated respectively with the third port for throttling fluid flow therethrough.

10. The throttled valve as claimed in claim 9, wherein said cam includes a second cam surface portion of a configuration for defining a second transfer function of the fluid flow rate different from said first mentioned transfer function.

11. The throttled valve as claimed in claim 10, wherein there is further included stops means for limiting the movement of said cam, whereby said first cam surface portion engages only said first needle valve and said second cam surface portion only engages said second needle valve.

12. The throttled valve as claimed in claim 8, wherein there is further included stop means for limiting the rotation of said cam to define a calibration point on said first cam surface portion.

13. The throttled valve as claimed in claim 12, wherein said calibration point defines a particular position of said cam and a corresponding position of said first needle valve with respect to said first port to determine a corresponding fluid flow rate through said first port.

14. The throttled valve as claimed in claim 13, wherein said corresponding flow rate is the maximum fluid flow rate through said first port.

15. The throttled valve as claimed in claim 8, wherein said first cam surface portion includes a first point of minimum radius and a second point of maximum radius and is generated in accordance with an Archimedean spiral such that the radius of said first cam surface increases as said cam rotates from said first to second points as the linear function of the angular rotation of said cam.

16. The throttled valve as claimed in claim 11, wherein said stop means limits the movement of said cam in a first direction to define a first calibration point on said first cam surface portion and limits the movement of said cam in a second direction opposite to said first direction for defining a second point on said second cam surface portion, said first and second calibration points activate said first and second needle valves to effect a maximum fluid flow rate through the first and third ports.

17. The throttled valve as claimed in claim 16, wherein each of said first and second cam surface portion is generated as an Archimedean spiral.

18. The throttled valve of claim 16 further comprising a second flexible arm on the cam follower spring biased such that the inside surface is disposed against the second cam surface and the outside surface is disposed against the second needle valve.

* * * * *

UNITED STATES PATENT AND TRADEMARK OFFICE
CERTIFICATE OF CORRECTION

PATENT NO.  : 5,094,260
DATED       : Mar. 10, 1992
INVENTOR(S) : Stuart, Peterson It is certified that error appears in the above-identified patent and that said Letters Patent is hereby corrected as shown below:

```
Column 3, line 2:   delete "Which" and insert --which--
Column 3, line 11:  delete "invention" and insert --invention,--
Column 4, line 16:  delete "!2" and insert --12--
Column 4, line 48:  delete "canote" and insert --connote--
Column 6, line 11:  delete "ward)y" and insert --wardly--
Column 7, line 11:  delete "25" and insert --28--
Column 7, line 13:  delete "25" and insert --28--
Column 7, line 15:  delete "25" and insert --28--
Column 7, line 18:  delete "25" and insert --28--
Column 11, line 10: delete "25" and insert --28--
Column 11, line 43: delete "trimmed and insert --trimmed.--
```

Signed and Sealed this

Twelfth Day of October, 1993

Attest:

BRUCE LEHMAN

*Attesting Officer*    *Commissioner of Patents and Trademarks*